United States Patent [19]

Fletcher

[11] 4,329,983

[45] May 18, 1982

[54] GUIDE DEVICE FOR ENDOTRACHEAL TUBES

[76] Inventor: Thomas S. Fletcher, 11002 W. 56th Ter., Shawnee Mission, Kans. 66203

[21] Appl. No.: 148,409

[22] Filed: May 9, 1980

[51] Int. Cl.³ ............................................. A61M 25/00
[52] U.S. Cl. .......................... 128/207.14; 128/207.15; 128/DIG. 9
[58] Field of Search ...................... 128/207.14, 207.15, 128/DIG. 9, 349 B, 349 R, 348

[56] References Cited

U.S. PATENT DOCUMENTS

| | | | |
|---|---|---|---|
| 3,416,531 | 12/1968 | Edwards | 128/DIG. 9 |
| 3,503,385 | 3/1970 | Stevens | 128/DIG. 9 |
| 3,552,384 | 1/1971 | Pierie et al. | 128/DIG. 9 |
| 3,802,440 | 4/1974 | Salem et al. | 128/DIG. 9 |
| 4,150,676 | 4/1979 | Jackson | 128/DIG. 9 |

FOREIGN PATENT DOCUMENTS 43-27685  11/1968  Japan .......................... 128/DIG. 9

OTHER PUBLICATIONS

Harris-Lake, Inc. Catalog-Laryngoscopes pp. 23-26. and Endotracheal Tubes pp. 40-41.

*Primary Examiner*—Henry J. Recla
*Attorney, Agent, or Firm*—Kokjer, Kircher, Bradley, Wharton, Bowman & Johnson

[57] ABSTRACT

A guide device for an endotracheal tube which assists in intubating the trachea. The guide device includes a flexible bar which may be inserted in the endotracheal tube. A flexible line extends along the bar and has a free length at the inner end of the bar. When the line is pulled, the free length shortens and causes the inner end portion of the bar to flex in bowed fashion against the endotracheal tube. This urges the tube forwardly toward the trachea and away from the esophagus.

3 Claims, 4 Drawing Figures

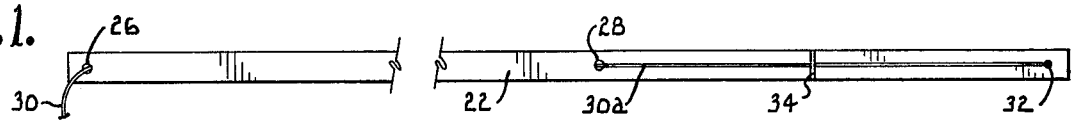
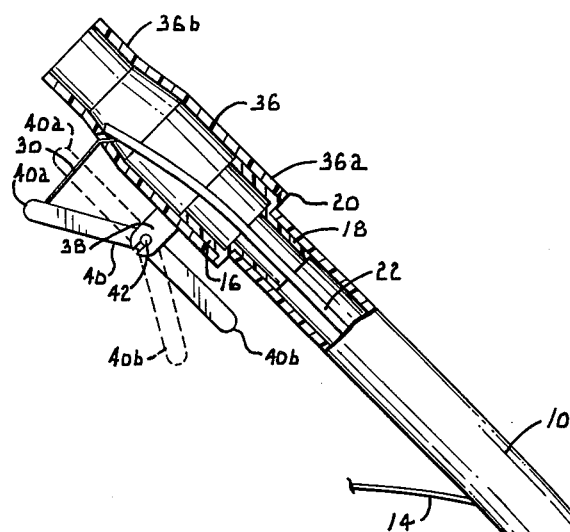
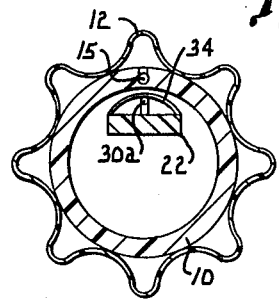
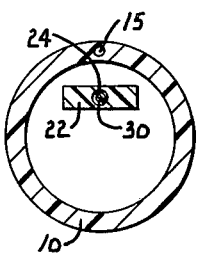
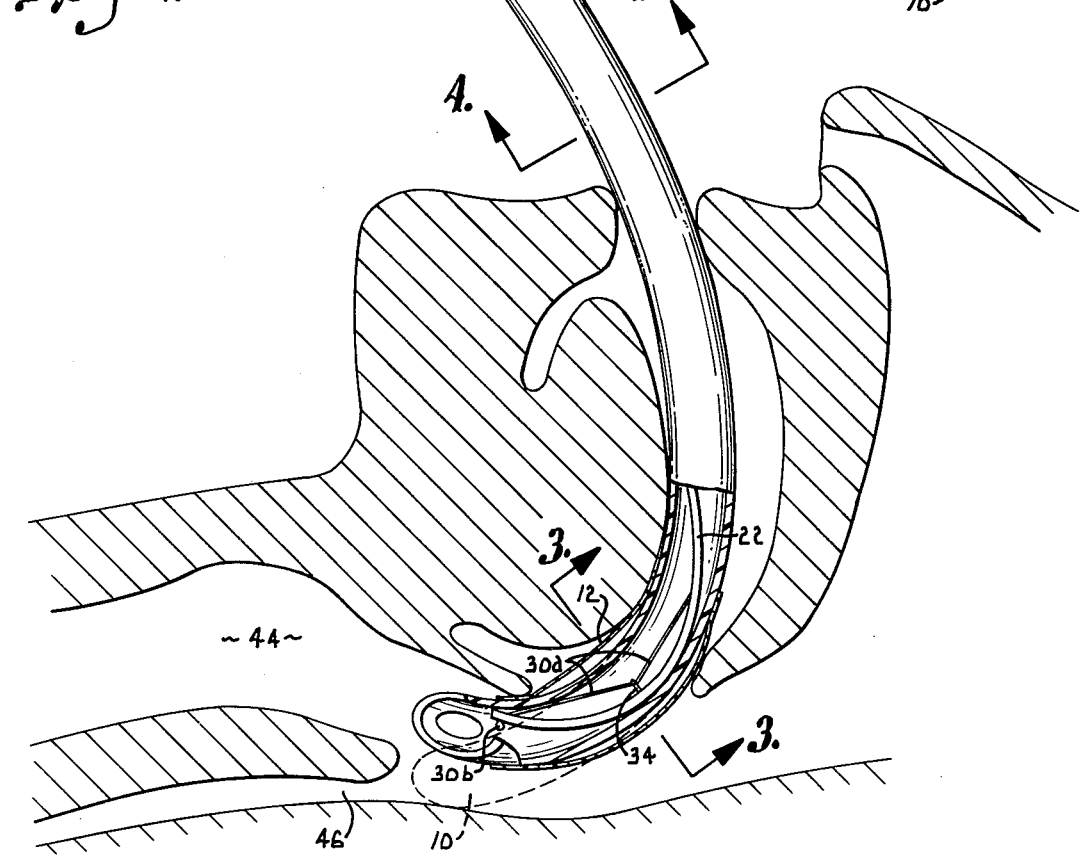

GUIDE DEVICE FOR ENDOTRACHEAL TUBES

BACKGROUND AND SUMMARY OF THE INVENTION

This invention relates generally to medical devices and more particularly to a device which provides assistance in intubating the trachea with an endotracheal tube.

Endotracheal tubes, commonly referred to as ET tubes, are widely used to supply air to the lungs of unconscious patients such as injured persons and patients undergoing operations. The ET tube is inserted into the nose or mouth of the patient, and its end is positioned in the trachea. The ET tube typically has an inflatable cuff or bladder which is expanded after insertion to seal the tube to the trachea. A respirator is then attached to the ET tube to supply air to the patient.

In order for the ET tube to function as intended, it must be properly applied to the trachea so that air can be directed through the tube and into the trachea. However, proper insertion of the tube is difficult to achieve, and it is not uncommon for the end of the ET tube to miss the trachea and instead be inserted into the esophagus which is located in back of the trachea. This is a particularly serious problem when intubating of the trachea is undertaken by inexperienced personnel. Even the most capable and experienced doctors sometimes fail to properly position the ET tube in the trachea, especially under the pressure of an emergency situation.

As can easily be appreciated, disastrous consequences can follow if the trachea is not intubated in the proper manner. Permanent brain damage and even death can result if the patient is deprived of air for even a short period of time. Where the patient is already seriously injured, failure to quickly provide air can severely compound the medical problems and significantly reduce the chance for successful recovery.

It is the primary object of the present invention to provide a device which assists in guiding an endotracheal tube toward the trachea in order to facilitate proper insertion of the tube.

Another object of the invention is to provide a device of the character described which is adapted for use with ET tubes of various sizes. The device can be constructed to fit virtually any size ET tube without requiring modification of the tube.

Yet another object of the invention is to provide a device of the character described which permits the ET tube to be accurately controlled during insertion. It is a particular feature of the invention that the ET tube can be easily and accurately guided past the epiglottis to facilitate intubating a patient with an anterior trachea.

A further object of the invention is to provide a device of the character described which can be easily operated with one hand during insertion of the ET tube, thereby freeing one hand for other activity.

An additional object of the invention is to provide a device of the character described which can be quickly and easily inserted into and removed from the ET tube. Once the ET tube is positioned properly, the guide device is withdrawn so that the ET tube can thereafter function in the usual manner.

Yet another object of the invention is to provide, in a device of the character described, an adapter fitting which permits ventilation of the patient immediately upon insertion of the ET tube.

A still further object of the invention is to provide a device of the character described which attaches snugly to the ET tube and which is flexible in order to conform with the curvature of the tube.

Still another object of the invention is to provide a device of the character described which is simple and economical to construct and use. The guide device is preferably formed from an inexpensive plastic substance such as polyethylene, and its cost is so small that it can simply be discarded after use.

Other and further objects of the invention, together with the features of novelty appurtenant thereto, will appear in the course of the following description.

DETAILED DESCRIPTION OF THE INVENTION

In the accompanying drawing which forms a part of the specification and is to be read in conjunction therewith and in which like reference numerals are used to indicate like parts in the various views:

FIG. 1 is a plan view of a flexible bar member which is included in a guide device constructed according to a preferred embodiment of the present invention, with the break lines indicating continuous length of the bar;

FIG. 2 is an elevational view of an endotracheal tube which is equipped with the guide device and which is in the process of being inserted into the trachea;

FIG. 3 is a sectional view on an enlarged scale taken generally along line 3—3 of FIG. 2 in the direction of the arrows; and FIG. 4 is a sectional view on an enlarged scale taken generally along line 4—4 of FIG. 2 in the direction of the arrows.

Referring now to the drawing in detail, numeral 10 designates a conventional endotracheal tube (ET tube) which is used to supply air to an unconscious patient. Tube 10 is formed from a soft plastic material and is gradually curved. The inner end portion of the ET tube has an inflatable cuff 12 which receives air from a small air line 14 equipped with a one way valve (not shown). Line 14 connects with a passage 15 (see FIGS. 3 and 4) which extends within the wall of tube 10 and leads to cuff 12. After the tube has been inserted into the trachea, cuff 12 is inflated to provide a seal with the trachea by supplying air through line 14 and passage 15 to the cuff. The opposite or outer end of tube 10 is provided with a fitting 16 having a neck portion 18 which is tightly inserted into the outer end of the tube. A flange 20 is formed on fitting 16.

In accordance with the present invention, a guide device is inserted into the endotracheal tube 10 in order to provide assistance in intubating the trachea. The guide device includes an elongate flexible bar 22 which is substantially the same length as the ET tube 10. Bar 22 is flat and is preferably formed of a material which is stiff enough to normally maintain the bar in a substantially straight condition and yet may be flexed relatively easily. Polyethlyene eva copolymer exhibits the requisite characteristics and is thus one material that can possibly be used. A channel in bar 22 is provided by a small passage 24 (FIG. 4) which may be formed in the bar by a profile extrusion process. As shown in FIG. 1, the outer end of passage 24 terminates in an opening 26 near the outer end of the bar, while another opening 28 forms the inner end of the passage at a location intermediate to the ends of the bar.

An elongate flexible line 30 extends slidably through passage 24 and is threaded through the openings 26 and 28. A free length 30a of line 30 extends generally along bar 22 from opening 28 to another opening 32 which is formed near the inner end of the bar. Line 30 is extended through opening 32 and is knotted at 30b (FIG. 2) to secure it to the inner end of bar 22. The free portion 30a of line 30 extends slidably through loop 34 which is attached to bar 22 at a location substantially midway between openings 28 and 32.

The outer end of line 30 extends slidably through an opening in the side of an adapter fitting 36 having a female end 36a which may be fitted closely around fitting 16. The outer end 36b of fitting 36 forms a male end to which a respirator or other ventilating device (not shown) may be connected.

The side of fitting 36 is provided with a pair of clasps 38 to which a small lever 40 is pivotally connected by a snap in pivot pin 42 molded with the lever 40. The lever 40 includes a pair of leg portions 40a and 40b which are angled relative to one another. The outer end of line 30 connects with lever 40 near the outer end of leg portion 40a at a location which is offset from pin 42. The lever is located farther from end 36b than the opening in fitting 36 which receives line 30. Consequently, application of pressure to leg portion 40b with the finger pivots lever 40 from the broken line position of FIG. 2 to the solid line position. This pulls line 30 and causes the inner end portion of bar 22 to bow, as will be more fully explained.

In use of the guide device, bar 22 is inserted into the ET tube 10, and fitting 36 is applied to fitting 16 in the manner shown in FIG. 2. The inner end of bar 22 is located adjacent the inner end of tube 10. The ET tube is then inserted into the mouth (or nose) of the patient such that its inner end approaches the trachea 44.

During insertion of the ET tube, pressure is applied to leg portion 40b and lever 40 is thereby pivoted away from the broken line position of FIG. 2 in order to pull line 30 outwardly. This pulling motion on the line effectively shortens portion 30a and thereby causes the inner end portion of bar 22 to curve or bow as shown in FIG. 2. The inner end of the bar is thus pulled against the inside wall of tube 10 in order to urge the inner end of the tube forwardly toward the trachea 44 and away from the esophagus 46. The guide device thus maneuvers the inner end of the ET tube toward the trachea 45 and away from the broken line position shown in FIG. 2 wherein the ET tube approaches the esophagus 46.

When the ET tube has been fully inserted into the trachea, cuff 12 is inflated to form a seal and a respirator or other ventilating device (not shown) is connected with the outer end 36b of fitting 36 in order to supply air to the trachea. After air has been supplied to the trachea through tube 10, the lungs are checked for ventilation, usually with the aid of a stethoscope, which verifies that the ET tube is properly positioned in the trachea. Once this has been verified, fitting 36 can be removed from fitting 16, and the bar 22 can be withdrawn from tube 10. The ventilating device can then be attached to the outer end of fitting 16, and the ET tube 10 thereafter functions to supply air to the trachea in the usual manner. The guide device is disposable and can be discarded after use.

Line 30 is slidably secured to bar 22 in extension along the length thereof, except for the free portion 30a of the line. Consequently, only the inner end portion of bar 22 between openings 28 and 32 is bowed when line 30 is pulled, since the remainder of the line simply slides within passage 24. Rather than extending through passage 24, line 30 can be loosely tied to bar 22 or slidably secured thereto in any other suitable manner. The loop 34 maintains the free portion 30a of the line relatively close to bar 22 while permitting portion 30a to shorten for maximum flexing of the bar 22 when the line is pulled.

Because only the inner end portion of bar 22 is bowed, the guide device effects curving of only the inner end portion of tube 10. Therefore, once the ET tube has been inserted far enough to pass the epiglottis, its inner end can be curved forwardly around the epiglottis and into the trachea with little difficulty. The farther lever 40 is pivoted away from the broken line position of FIG. 2, the greater the degree of curvature of the inner end portion of tube 10, and the lever thus provides accurate control of the ET tube during insertion.

It is thus apparent that the guide device assists in intubating the trachea in a safe and effective manner. The simplicity of the device permits even inexperienced medical personnel to properly insert the ET tube 10 into the trachea, rather than into the esophagus as sometimes occurs when the ET tube is inserted without a guide device. The guide device facilitates proper insertion of the endotracheal tube under direct vision (using a Laryngoscope or the like), under conditions of restricted visibility with difficult patients, and also under conditions of blind intubation without the aid of any introducing equipment. External introducing devices such as forceps and the like are not needed. The guide device also eliminates the problems associated with internal malleable type introducers (copper stylets and the like), because the guide device contours anatomically to prevent trauma and also because it is properly formed after insertion to eliminate deviation during insertion.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawing is to be interpreted as illustrative and not in a limiting sense.

Having thus described the invention, I claim:

1. In a device for intubating the trachea, the combination of:

an elongate endotracheal tube of flexible construction adapted to intubate the trachea, said tube having one end portion insertable into the trachea and an opposite end portion which remains outside of the body during intubation;

an elongate flexible bar member disposed within said tube and having a length to extend substantially between said end portions of the tube, said bar member having a first end located adjacent said one end portion of the tube and a second end located adjacent said opposite end portion of the tube;

a fitting removably attached to said second end portion of the tube and adapted for connection with an air source to direct air into the endotracheal tube, said fitting having a side portion;

an elongate flexible line extending generally along the length of said bar member and having one end connected with said first end of the bar member and an opposite end extending slidably through said side portion of the fitting and adapted to be pulled from the exterior of the endotracheal tube with the second end of said bar member contacting the fitting to retain the bar member in said tube when said line is pulled, said line having a slidable connection with said bar member at a preselected location thereon spaced from said first end of the bar member to provide a free length of the line between said first end of the bar member and said preselected location; and means for establishing a sliding connection of said line with said bar member at a location between said first end of the bar and said preselected location, whereby pulling of said opposite end of the line shortens said free length of the line to effect bowing of said bar member between said first end and said preselected location to engage the bar member against said tube in a manner to curve said one end portion of the tube toward the trachea, said sliding connection holding the line adjacent said bar member to effect smooth bowing of the bar member between said first end portion and said preselected location.

2. The combination set forth in claim 1, wherein said establishing means comprises a loop attached to said bar member between said first end and said preselected location, said free length of the line extending slidably through said loop.

3. The combination set forth in claim 1, wherein:

said bar member is a solid member having a passage therein extending substantially between said second end and said preselected location; and said line extends loosely through said passage and extends out of the passage adjacent said second end of the bar member.

* * * * *